United States Patent [19]

Hufnagel

[11] 4,414,721

[45] Nov. 15, 1983

[54] OCCLUSIVE CLIP AND APPLICATOR FOR CONSTRICTING FLEXIBLE TUBULAR MEMBERS

[76] Inventor: Charles A. Hufnagel, 4900 Massachusetts Ave., NW., Washington, D.C. 20016

[21] Appl. No.: 204,831

[22] Filed: Nov. 7, 1980

[51] Int. Cl.³ .................. A61B 17/12; A61B 17/00
[52] U.S. Cl. .................................... 128/325; 128/346
[58] Field of Search ........... 128/325, 346, 319, 334 R, 128/334 C, 335

[56] References Cited

U.S. PATENT DOCUMENTS

| | | |
|---|---|---|
| 600,887 | 3/1898 | Pettit . |
| 1,361,338 | 12/1920 | Ketchum . |
| 1,552,495 | 9/1925 | Mohr . |
| 1,708,432 | 4/1929 | Sprigg . |
| 2,123,890 | 7/1938 | Gossrau .......................... 128/325 |
| 2,307,377 | 1/1943 | Riccardi .......................... 128/346 |
| 2,384,697 | 9/1945 | Riccardi .......................... 128/346 |
| 2,434,831 | 1/1948 | Brandenburg . |
| 2,598,901 | 6/1952 | Garland . |
| 2,635,238 | 4/1953 | Garland . |
| 2,796,065 | 6/1957 | Kapp ............................... 128/346 |
| 3,040,749 | 6/1962 | Payton . |
| 3,155,095 | 11/1964 | Brown ........................... 128/334 C |
| 3,175,556 | 3/1965 | Wood et al. . |
| 3,204,636 | 9/1965 | Kariher et al. . |
| 3,247,852 | 4/1966 | Schneider ....................... 128/346 |
| 3,270,745 | 9/1966 | Wood . |
| 3,363,628 | 1/1968 | Wood . |
| 3,463,156 | 8/1969 | McDermott . |
| 3,586,002 | 6/1971 | Wood ............................. 128/346 |
| 3,899,914 | 8/1975 | Akiyama . |
| 3,954,108 | 5/1976 | Davis . |
| 3,978,555 | 9/1976 | Weisenthal . |

FOREIGN PATENT DOCUMENTS 1957855 5/1971 Fed. Rep. of Germany .
2525650 12/1976 Fed. Rep. of Germany .

Primary Examiner—C. Fred Rosenbaum
Assistant Examiner—C. W. Shedd
Attorney, Agent, or Firm—Schuyler, Banner, Birch, McKie & Beckett

[57] ABSTRACT

An occlusive clip adapted to be compressed about and constrict a flexible tubular member comprises a pair of opposed striplike clamping legs joined together at one end and adapted to receive the tubular member therebetween. The legs have a plurality of discrete apertures formed therethrough and spaced therealong providing relief areas for the material of the compressed tubular member to stabilize the clip and prevent migration thereof. The clip legs may also be corrugated to provide additional points of fixation and enhance the three dimensional stability of the clip. An applicator for the clip has jaws which are contoured to matingly receive the legs of the clip and securely hold them in position.

16 Claims, 13 Drawing Figures

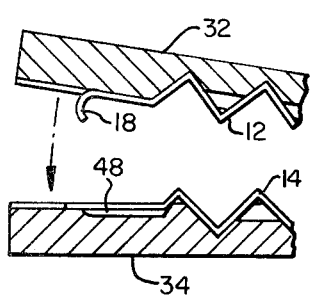
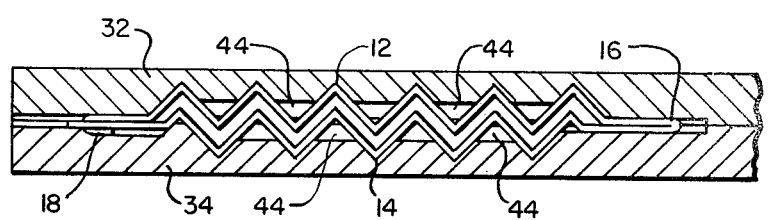
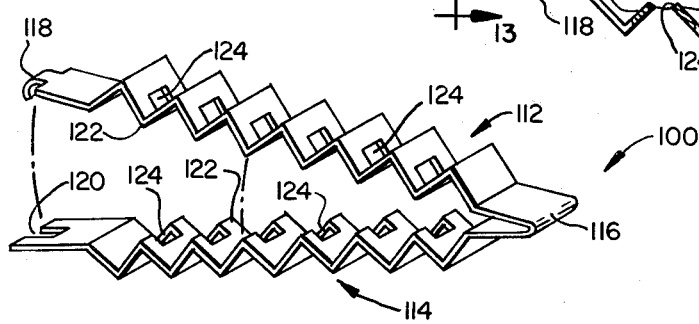
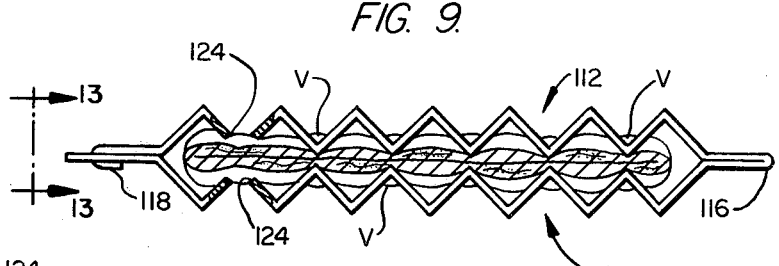
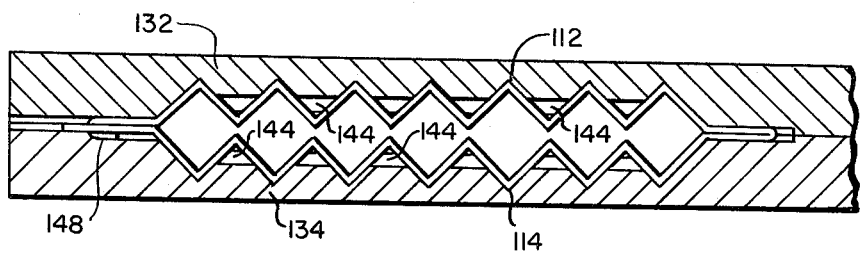
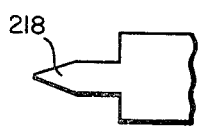
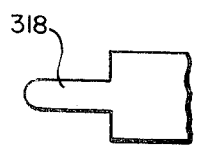
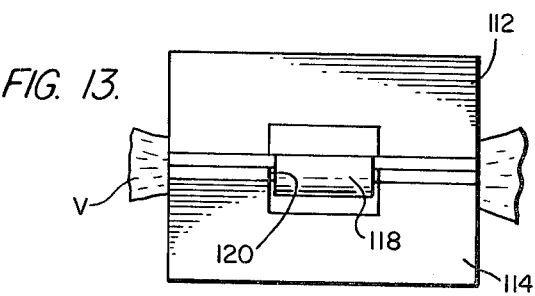

OCCLUSIVE CLIP AND APPLICATOR FOR CONSTRICTING FLEXIBLE TUBULAR MEMBERS

TECHNICAL FIELD

The invention relates to clips for constricting flexible tubular members, and applicators therefor. These clips are used to close off the flow of fluid through various types of flexible tubular members, and are particularly useful in surgical applications to stop the flow of a bodily fluid through a tubular biological structure such as a blood vessel or the like. Clips such as these are used in lieu of ligatures in order to substantially reduce the amount of time required to perform surgical procedures.

BACKGROUND ART

The prior art literature discloses a wide variety of clamps and clips for constricting flexible tubular members of many different types. In the surgical field many different types of vascular clamps and clips have been used by medical practitioners for quite some time. The use of hemostatic clips for tying off blood vessels in lieu of ligatures has become widespread in recent years. An example of a clip of this type is disclosed in Wood U.S. Pat. No. 3,363,628. Such hemostatic clips are manufactured in different sizes for application to blood vessels of varying size. The clips are formed of a nontoxic material which can be readily bent by a forceps-type applicator, and retain their bent shape when compressed about a blood vessel or other vascular structure. Most clips on the market at the present time are metallic, predominantly tantalum. The applicator is a simple forceps with grooves in the end of the instrument which hold the clip in place by friction.

The reliability of currently used vascular clips is often somewhat questionable. Slippage (migration) along the vessel frequently occurs. The clip ends may separate due to the pressure exerted by the fluid within the vessel, causing the clip to slide sideways off the vessel. The consequences of a clip failure can be quite serious.

DISCLOSURE OF THE INVENTION

In accordance with the present invention, an occlusive clip adapted to be compressed about and constrict a flexible tubular member comprises a pair of opposed clamping legs joined together at one end and adapted to receive the tubular member therebetween. The opposed inner surfaces of the leg are corrugated with the crests and valleys of the corrugations extending generally transversely of the length of the legs. The opposed inner surfaces of the legs have a plurality of discrete slots spaced along the legs providing relief areas for the material of the compressed tubular member. This structure stabilizes the clip and prevents its migration along the tubular member. The clip preferably includes locking means for securing the free ends of the legs together to lock the clip in a closed position.

The invention also encompasses an occlusive clip comprising a pair of opposed, strip-like clamping legs joined together at one end, wherein the legs have a plurality of discrete apertures formed therethrough and spaced therealong providing relief areas for the material of the compressed tubular member. The apertures may be combined with corrugations on the legs of the clip to firmly engage the tubular member and prevent migration of the clip. Locking means also may be provided for securing the free ends of the clip together.

The invention further includes an applicator for the clip which comprises a pair of opposed clip-engaging jaws movable relative to one another between an open clip loading position and a closed clip compressing position, the opposed inner surfaces of the jaws being contoured to generally conform to the outer surfaces of the clamping legs of the clip. These inner jaw surfaces are interrupted by depressed areas in registry with the clip apertures to accommodate the material of the compressed tubular member which is forced through the apertures when the clip is compressed.

The invention further includes a combined clip and applicator for use in constricting a flexible tubular member.

BRIEF DESCRIPTION OF THE DRAWINGS

The details of the invention will be described in connection with the accompanying drawings, in which:

FIG. 6 is a partial sectional view of the applicator with a clip positioned therein illustrating the manner in which the clip is compressed and locked by the applicator;

FIG. 7 is a side elevational view in section of the clip of FIG. 1 in its closed position within the applicator;

FIG. 8 is a perspective view of a second embodiment of the clip of the invention;

FIG. 9 is a side elevational view, partly in section, of the clip of FIG. 8 applied to a blood vessel;

FIG. 10 is a side elevational view in section of the clip of FIG. 8 in its closed position within the applicator;

FIG. 11 is a plan view of the free end of one leg of the clip having a pointed locking prong;

FIG. 12 is a plan view of the free end of one leg of the clip having a rounded locking prong; and FIG. 13 is an end elevational view of the second embodiment of the clip taken along line 13—13 of FIG. 9.

BEST MODE FOR CARRYING OUT THE INVENTION

In the description that follows the clip and applicator according to the invention are described in connection with the obstruction of blood vessels and other vascular biological structures. It is to be understood, however, that the clip and applicator of the invention are capable of being used in connection with flexible tubular members of any type.

Figure 1:
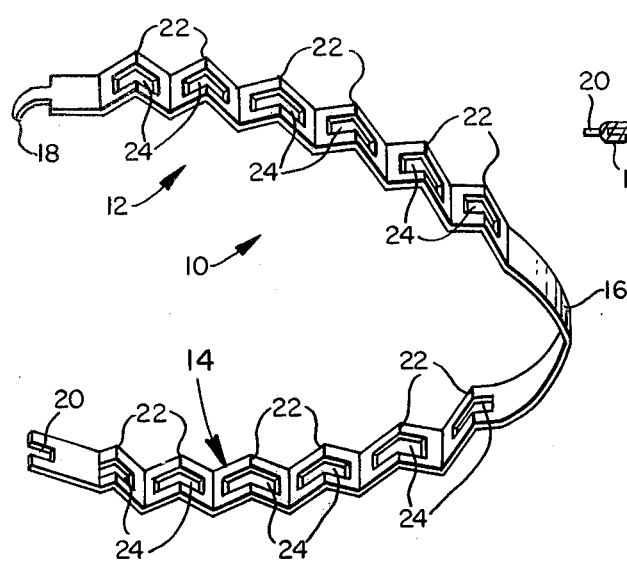
FIG. 1 is a perspective view of one embodiment of the clip according to the invention.
Figure 3:
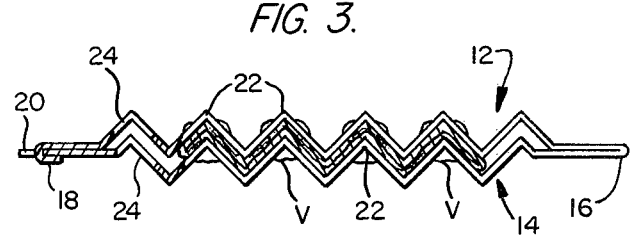
FIG. 3 is a sectional view taken along line 3—3 of FIG. 2.
Figure 2:
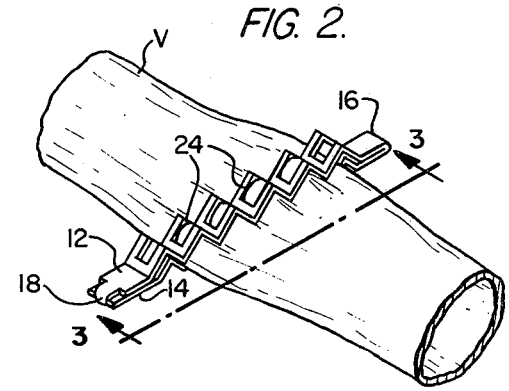
FIG. 2 is a perspective view of the clip of FIG. 1 applied to a blood vessel.
Figure 4:
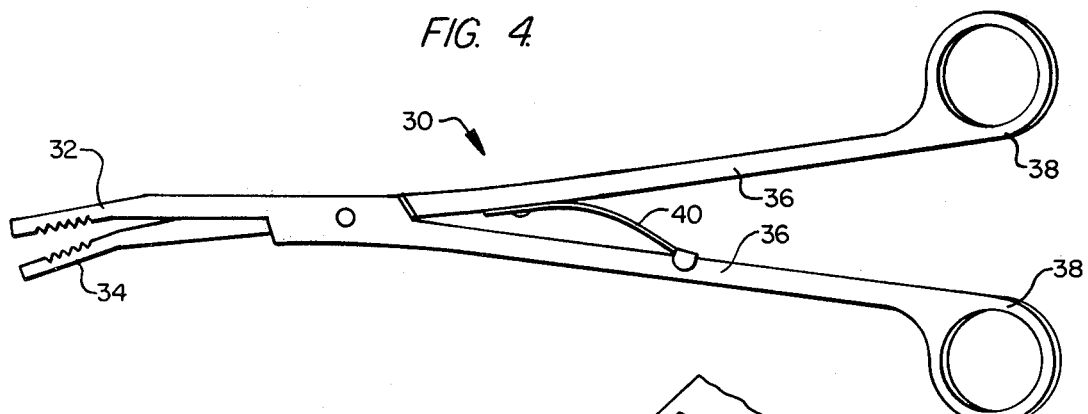
FIG. 4 is a side elevational view of a forceps-like applicator for applying the clips of the invention to flexible tubular members.

Refering to FIGS. 1, 2 and 3, one form of clip 10 according to the invention is formed of a strip of material and has legs 12 and 14 which are joined together at one end 16. The free end of leg 12 is provided with a locking prong 18, while the free end of leg 14 is provided with a locking notch 20 which is sized to receive prong 18 in a manner described below. Legs 12 and 14 are corrugated to form crests and valleys which interdigitate with one another when the clip is compressed and closed. Alternating crests 22 of each leg are provided with slots or apertures 24 which are in registry with one another when the clip is closed. Slots or apertures 24 provide tissue relief areas into which the blood vessel extends when it is compressed between the legs of the clip.

Figure 5:
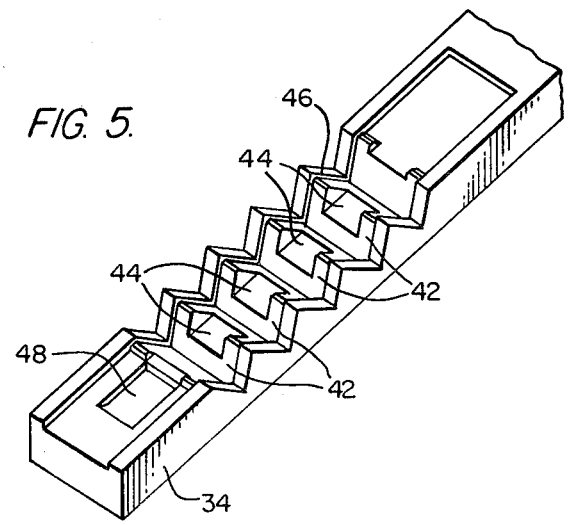
FIG. 5 is a perspective view of a portion of one jaw of the applicator of FIG. 4.

Referring to FIGS. 4 through 7, the applicator according to the invention is a forceps-like device 30 comprising a pair of relatively articulated jaws 32 and 34 which are secured to handles 36 having finger grip portions 38. Handles 36 are urged apart by a leaf spring 40. With the exception of the configuration of the jaws 32 and 34, this applicator is of conventional construction and is similar to, for example, that disclosed in Woods U.S. Pat. No. 3,270,745. The opposed inner surfaces of jaws 32 and 34 are corrugated to matingly receive the legs 12 and 14, respectively, of clip 10. FIG. 5 shows the lower jaw 34 of applicator 30. The crests 42 of the corrugations in jaw 34 are interrupted by slots 44 which are in alignment with the slots or apertures 24 of clip leg 14 to provide space into which the extruded tissue may extend when compressed between the legs of the clip. The sides of jaw 34 are provided with a slightly raised shoulder 46 which prevents lateral movement of the clip when in position between the jaws. An anvil slot 48 is provided near the tip of jaw 34 for bending locking prong 18 of the clip rearwardly against the bottom side of the end of leg 14 after it is guided through notch 20. Upper jaw 32 is similarly configured, except that it does not have an anvil slot.

In use, a clip is inserted between the jaws of the applicator and the clip is positioned around the vessel to be obstructed. When properly positioned, the handles 36 of the applicator are squeezed together, causing jaws 32 and 34 to converge. This conversion compresses legs 12 and 14 of the clip together and causes locking prong 18 to enter notch 20 and be bent by anvil slot 48 around and beneath the end of leg 14 to lock the clip in a closed position. As the legs of the clip are compressed, the vessel is constricted and portions of the vessel protrude through the slots or apertures 24 in the clip into the slots 44 in the jaws. After compression the jaws 32 and 34 are opened and the applicator is removed from the compressed clip.

A second embodiment of the clip according to the invention, particularly well suited for obstructing larger vessels, is illustrated in FIGS. 8, 9, 10 and 13. The jaws of an applicator for use with such a clip are illustrated in FIG. 10. Clip 100 has legs 112 and 114 joined together at one end 116. Leg 112 has a locking prong 118, while leg 114 has a locking notch 120. Legs 112 and 114 are corrugated but, in contrast to the embodiment of FIG. 1, the crests 122 of these corrugations oppose one another when the clip is closed. Alternating corrugations are provided with slots or apertures 124 through which vessel tissue extends when the clip is compressed. Jaws 132 and 134 of applicator 130 are corrugated such that the jaws matingly receive the corrugated legs of clip 100. The jaws also have tissue receiving slots 144. An anvil slot 148 is provided in lower jaw 134. The method of use of this applicator and clip is substantially the same as that described in connection with the clip and applicator of the first embodiment. Of course, the relative positions of the corrugations will differ.

FIGS. 11 and 12 illustrate different configurations for the locking prong which may be used in conjunction with either embodiment of the clip. Prong 218 has a sharply pointed tip which makes it particularly well suited for piercing the tissue surrounding the vessel to be obstructed during the compression of the clip, to add stability to the entire installation. Prong 318 has a rounded tip for applications where tissue piercing is not required.

The clip according to the invention may be constructed of any biologically inert and suitably ductile material such as tantalum, silver, stainless steel, and various plastics, to name just a few. The clip must be sufficiently strong to holds its final shape once it is compressed and locked in a closed position. The clip may be manufactured in various sizes for use on vessels of different size. For example, clips having legs ranging in length from 3 millimeters to 10 millimeters probably would suffice for most surgical applications. Typical leg widths range from about 0.3 millimeters to 3 millimeters. Minimum leg thickness for a tantalum clip would be approximately 0.2 millimeters. Of course, other sizes may also be manufactured. Although the striplike leg configuration is preferred, it is contemplated that a clip according to the invention having the required corrugations and/or apertures or slots on its tissue-engaging surfaces may be manufactured with legs which are thicker than those illustrated in the figures.

The tissue relieving slots or apertures formed in each leg of the clip serve to prevent longitudinal slippage or migration of the clip along the vessel to be occluded, and minimize any tendency of the clip to cut through the vessel. The corrugations prevent lateral slippage of the clip and, together with the slots or apertures, provide multiple points of fixation which yield superior three dimensional stability to the clip when compressed about the vessel.

The open shape of the clip preferably has a generally C-shaped configuration, such as that shown in FIG. 1. However, other configurations may also be used. For example, the clip may have a V-shaped configuration such as that shown in FIG. 8. Or, the clip may be U-shaped. An advantage of a C-shaped or U-shaped clip is that the locking prong and notch at the free ends of the clip legs are approximated first before the legs converge, thereby ensuring entrapment of the vessel. The notch guides the prong into this position so that the free ends of the legs are properly positioned relative to one another before the vessel itself is completely constricted.

The applicator may be fabricated of any suitable biologically inert material, such as stainless steel or plastic. The applicator can be modified to accomodate a clip magazine, either permanent or disposable, as is conventionally known in the art.

It will be obvious to one of ordinary skill that numerous modifications may be made without departing from the true spirit and scope of the invention, which is to be limited only by the appended claims.

I claim:

1. An occlusive clip configured to be compressed about and constrict a flexible tubular member, comprising a pair of opposed strip-like clamping legs hingedly interconnected at one end and adapted to receive a tubular member therebetween, the opposed inner surfaces of said legs being corrugated to present undulating surfaces of crests and valleys extending generally transversely of the length of said legs with the crests and valleys of one leg being prearranged with respect to the crests and valleys of the other leg, and at least one slot means in each of said legs for providing a relief area for the material of the compressed tubular member to stabilize the clip and prevent migration thereof.

2. A clip according to claim 1 wherein said slots are apertures.

3. A clip according to claim 1 wherein the crests of said legs are prearranged to interdigitate when the clip is compressed, and said slots are discrete slots located in the crests of one leg and in the valleys of the other leg.

4. A clip according to claim 3 wherein said slots are apertures.

5. A clip according to claim 1 wherein the crests of said legs are prearranged to align when the clip is compressed, and said slots are discrete slots located in the crests of both legs.

6. A clip according to claim 5 wherein said slots are apertures.

7. A clip according to claim 1 further comprising locking means for securing the free ends of said legs together to lock the clip in a closed position constricting the tubular member.

8. A clip according to claim 7 wherein said locking means comprises a notch in the free end of one leg and a prong at the free end of the other leg which is adapted to be inserted into said notch and bent over when the clip is closed.

9. In combination, an occlusive clip adapted to be compressed about and constrict a flexible tubular member, and an applicator therefor, said clip comprising a pair of opposed, corrugated, strip-like clamping legs hingedly interconnected at one end and adapted to receive a tubular member therebetween, said legs having undulating inner and outer surfaces of crests and valleys extending generally transversely of the length of said legs with the crests and valleys of one leg being prearranged with respect to the crests and valleys of the other leg, and at least one aperture in each of said legs for providing a relief area for the material of the compressed tubular member to stabilize the clip and prevent migration thereof, and said applicator comprising a pair of opposed clip-engaging jaws movable relative to one another between an open clip loading position and a closed clip compressing position, the opposed inner surfaces of said jaws being corrugated with crests and valleys which conform to the outer surfaces of the clamping legs of the clip, interrupted by depressed areas in registry with said clip apertures to accommodate the material of the compressed tubular member which is forced through said apertures when the clip is compressed.

10. A clip and applicator combination according to claim 9 wherein said aperatures in said clip legs are located in the inwardly directed crests of the corrugations, said depressed areas comprising notches in the corresponding crests of the corrugations on said applicator jaws.

11. A clip and applicator combination according to claim 10 further comprising a pair of raised shoulders flanking the corrugations on each jaw for preventing lateral shifting of said clip in said applicator.

12. A clip and applicator combination according to claim 11, wherein said clip further comprises a locking prong at the free end of one of said legs and a locking notch at the free end of the other leg adapted to receive said locking prong, and wherein said applicator further comprises an anvil underlying said locking notch for bending said locking prong over in said locking notch to lock said clip legs in a closed position constricting said tubular member.

13. An applicator for compressing an occlusive clip about a flexible tubular member, the clip comprising a pair of opposed, corrugated, strip-like clamping legs hingedly interconnected at one end and adapted to receive a tubular member therebetween, the legs having undulating inner and outer surfaces of crests and valleys extending generally transversely of the length of the legs with the crests and valleys of one leg being prearranged with respect to the crests and valleys of the other leg, and at least one aperture in each of the legs for providing a relief area for the material of the compressed tubular member to stabilize the clip and prevent migration thereof, said applicator comprising a pair of opposed clip-engaging jaws movable relative to one another between an open clip loading position and a closed clip compressing position, the opposed inner surfaces of said jaws being corrugated with crests and valleys which conform to the outer surfaces of the clamping legs of the clip, interrupted by depressed areas in registry with said clip apertures to accommodate the material of the compressed tubular member which is forced through said apertures when the clip is compressed.

14. An applicator according to claim 13 wherein the apertures in the clip legs are located in the inwardly directed crests of the corrugations, said depressed areas comprising notches in the corresponding crests of the corrugations on said applicator jaws.

15. An applicator according to claim 14 further comprising a pair of raised shoulders flanking the corrugations on each jaw for preventing lateral shifting of the clip in the applicator.

16. An applicator according to claim 15, wherein the clip has a locking prong at the free end of one of the legs and a locking notch at the free end of the other leg adapted to receive the locking prong, and wherein the applicator further comprises an anvil in one jaw adapted to underlie the locking notch for bending the locking prong over in the locking notch to lock the clip legs in a closed position constricting the tubular member.

* * * * *